United States Patent
Witte et al.

(10) Patent No.: US 6,882,886 B1
(45) Date of Patent: Apr. 19, 2005

(54) VESSEL ELECTRODE LINE

(75) Inventors: Joachim Witte, Berlin (DE); Erhard Flach, Berlin (DE); Herman Rexhausen, deceased, late of Hildesheim (DE); by Alfred Zmarzlik, legal representative, Eschweiler (DE); by Johannes Schulz, legal representative, Trostberg (DE); by Dietmar Schulz, legal representative, Essen (DE); by Dieter Schulz, legal representative, Düsseldolf (DE); by Barbara Schulz, legal representative, Düsseldorf (DE); by Helmut Schulz, legal representative, Hildesheim (DE); by Oskar Schulz, legal representative, Bonn (DE); by Edith Galisch, legal representative, Hildesheim (DE); by Johanna Polinowski, legal representative, Dortmund (DE); by Waltraud Schulz, legal representative, Dortmund (DE); by Margarete Speck, legal representative, Frankfurt am Main (DE)

(73) Assignee: Therapiegeraete GmbH & Co. Ingenieurbuero Berlin, Berlin (DE)

( * ) Notice: Subject to any disclaimer, the term of this patent is extended or adjusted under 35 U.S.C. 154(b) by 0 days.

(21) Appl. No.: 09/296,133

(22) Filed: Apr. 22, 1999

(Under 37 CFR 1.47)

(30) Foreign Application Priority Data

Apr. 22, 1998 (DE) .......................................... 198 18 908
Aug. 18, 1998 (DE) .......................................... 198 38 360

(51) Int. Cl.⁷ ................................................. A61N 1/05
(52) U.S. Cl. ..................................................... 607/122
(58) Field of Search ................................. 607/120, 121, 607/122, 126, 127

(56) References Cited

U.S. PATENT DOCUMENTS

| 3,664,347 A | | 5/1972 | Harmjanz |
| 4,026,303 A | * | 5/1977 | Babotai ...................... 128/418 |
| 4,332,259 A | | 6/1982 | McCorkle, Jr. |
| 4,550,737 A | | 11/1985 | Osypka |
| 5,002,067 A | * | 3/1991 | Berthelsen et al. ......... 128/786 |
| 5,405,374 A | | 4/1995 | Stein |
| 5,423,884 A | * | 6/1995 | Nyman et al. ............... 607/127 |
| 5,476,498 A | | 12/1995 | Ayers |
| 5,571,159 A | | 11/1996 | Alt |
| 5,628,779 A | | 5/1997 | Bornzin et al. |
| 5,653,734 A | | 8/1997 | Alt |

FOREIGN PATENT DOCUMENTS

| DE | 30 49 652 | 2/1982 |
| EP | 0 085 417 | 8/1983 |
| EP | 0 584 525 | 3/1994 |
| EP | 0 566 652 | 6/1994 |
| EP | 0 601 338 | 6/1994 |
| EP | 0 601 339 | 6/1994 |
| EP | 0 601 340 A1 | 6/1994 |
| EP | 0 606 688 | 7/1994 |
| EP | 0 788 808 | 8/1997 |
| JP | 5 49701 | 3/1993 |
| WO | WO 92/11898 | 7/1992 |

* cited by examiner

*Primary Examiner*—William E. Kamm
(74) *Attorney, Agent, or Firm*—Venable LLP; Robert Kinberg

(57) ABSTRACT

A vessel electrode line (10) for pacemaker stimulation and/or for sensing cardiac actions in the region of the atrium has an oblong base body (11) that receives at least one electrode supply line, and at least one electrode (13, 14) that is mounted on the base body, with the effective diameter of the electrode(s) being nearly identical to the diameter of the base body, and with fixing elements (11a) that essentially do not act as an electrode, and particularly have at least a partial insulating surface, being provided for fixedly positioning the electrode(s) with respect to the vessel wall.

16 Claims, 9 Drawing Sheets

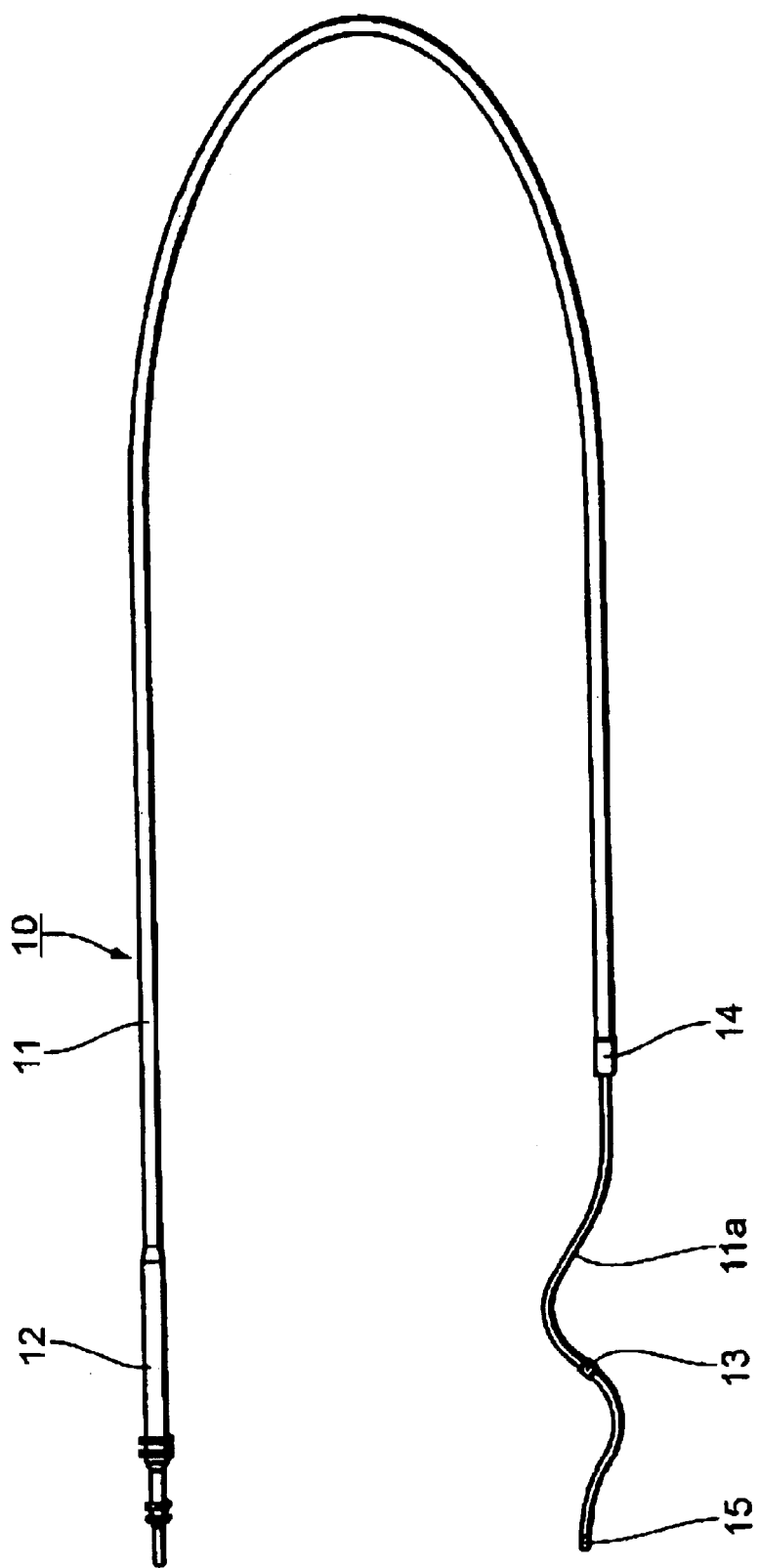

VESSEL ELECTRODE LINE

BACKGROUND OF THE INVENTION

The invention relates to a vessel electrode line for a cardiac pacemaker.

In the therapy of different chronic cardiac irregularities, implanted cardiac pacemakers have long been used in connection with stimulation electrodes disposed on an intracardiac electrode catheter and positioned on the inner wall of the heart; these electrodes stimulate the excitable heart tissue, thereby compensating for a defect in the endogenous cardiac impulse formation and conduction system.

The design of the electrode lines has been repeatedly improved. With the objective of long-term assurance of a good contact between the stimulation electrode(s) and the heart tissue, and in the interest of an energy-saving, reliable stimulation, numerous technical solutions have been found for anchoring the electrode lines to the heart wall, both in the ventricle as well as in the atrium, and fundamental, practical improvements have been made successfully.

Electrode lines, especially for implantable defibrillators, have also been proposed; these lines are inserted into large vessels near the heart, and impart the defibrillation energy to the vessel wall.

EP 0 601 338 A1 describes such an electrode system for an implanted defibrillator, having at least two intravascular coil electrodes (spiral-shaped electrodes) that are held in place by virtue of their size, and have no special anchoring means. One of these large-surface defibrillation electrodes can be disposed in the vena cava superior, while a further one can be disposed in the coronary sinus.

U.S. Pat. No. 5,571,159 describes a temporary catheter for atrial defibrillation, which has, in addition to a first, spiral-shaped electrode section positioned in the atrium, a second electrode section, which is positioned in the pulmonary artery, as well as an inflatable balloon at the distal end for positioning the electrodes.

EP 0 566 652 B2 describes an electrode configuration that is designed in the manner of a stent and can be expanded by a dilation balloon; it is used as a defibrillation electrode in a blood vessel, especially in the coronary sinus.

For special applications, such as so-called bi-atrial or multi-site stimulation, it can be useful to position pacemaker stimulation or sensing electrodes in a vessel near the heart, particularly in the coronary sinus, because an electrode implantation in the left atrium is particularly problematic. The known, large-surface defibrillation electrodes are fundamentally unsuitable for this purpose.

SUMMARY OF THE INVENTION

It is therefore the object of the invention to provide a vessel electrode line of the generic type mentioned at the outset, which is suitable for pacemaker stimulation or the sensing of cardiac actions.

This object is accomplished by a vessel electrode line for at least one of pacemaker stimulation and sensing cardiac actions in a region of an atrium, including an oblong base body; at least one electrode supply line received in the base body; at least one electrode mounted on the base body and having an effective diameter nearly identical to the diameter of the base body; and fixing elements that essentially do not act as an electrode, and which have at least a partial insulating surface, for fixedly positioning the at least one electrode with respect to the vessel wall.

The invention encompasses the concept of realizing a vessel electrode line having at least one small-surface electrode and fixing elements that are adapted to the vessel configuration, with which stimulation impulses can be transmitted to the vessel wall, or cardiac-action potentials can be tapped, in an efficient manner and with exact positioning.

For realizing this concept, the proposed electrode line includes an electrode or electrodes whose effective diameter (as is known from intracardiac electrode arrangements) is nearly identical to the diameter of the base body, and fixing elements, which do not act as an electrode (and particularly have an insulating surface) for fixedly positioning the electrode(s) with respect to the vessel wall.

The fixing elements of the proposed vessel electrode line differ in shape from those of electrode lines to be anchored in intracardiac fashion, but differ at least in dimension, because they do not serve to fix the line by anchoring it in relatively thick muscle tissue or in the trabecula structure of the ventricle. Rather, the fixing is based on either an elastic tension against the vessel wall or, alternatively, on the penetration into the wall or branches of a secondary vessel.

In accordance with the first alternative, the fixing elements encompass an essentially coplanar section of the base body that is given a preset sinusoidal shape, or a section of the base body that is elastically pre-shaped as a helix on the jacket surface of a cylinder having an elliptical base. The base body preferably has (in the relaxed state) a lateral extension of two to five times the diameter of the base body, and an elasticity that is matched to that of the vessel wall. It has a longitudinal extension that usefully encompasses more than one sinus period, or more than a complete turn around the cylinder jacket, in the interest of secure positioning with the avoidance of high local stressing of the vessel wall.

In the embodiment of the second alternative, flexible fixing elements that are mounted to the distal end of the base body for fixing the line in the aforementioned lateral vessel (especially the coronary sinus) have a lateral extension that is matched to the vessel's diameter, and the base body has a high degree of flexibility in this region for permitting easy bending into the lateral vessel.

A fixing element of this type preferably comprises a plastic helical-thread section that surrounds the distal end of the base body and has one or more turns, and is particularly made of the same material as the base body, and can be used to fix the electrode line actively in a small, venous lateral vessel of the coronary sinus. While this element is extensively sealed by the "screwing in" of the electrode line, the resulting congestion is tolerable in a lateral vessel.

As an alternative to the latter embodiment, the base body can support a plurality of plastic "fins" that are resiliently inclined, with respect to the longitudinal axis of the base body, toward the proximal end; these fins can passively anchor the vessel electrode line in branches of the pericardial vessel system. The dimensions of the fins are larger than in similar arrangements that are anchored in the trabecula structure of the ventricle to match the other body surroundings.

An elastic helix that can be stretched during the insertion, or a tubular or annular hollow body that can be expanded in the manner of a stent following insertion and has final dimensions that are adapted to the vessel diameter, also represents a suitable fixing element.

It is advantageous when the electrically-active surface remains relatively small. This can be attained either by at least partial insulation of the surface, or at least partial construction from a non-conductive material, or by minimal dimensioning of the entire fixing element. The electrodes can be positioned on the line such that (in a unipolar line) the electrode or (in a bipolar or multipolar line) the most distal of several electrodes is spaced between 30 and 80 mm from the distal end of the base body, which assures a stable orientation of the electrode(s) relative to the vessel wall in the implanted state in connection with a curved course of the base body that is matched to this spacing. Correspondingly, in a bipolar line, the electrode spacing is between 30 and 80 mm. The use of a point electrode is also possible, either alone or in combination with a ring electrode.

The first and/or second stimulation electrode(s) preferably has (have) a geometric surface area in a range between 10 and about 25 mM$^2$, and particularly a fractal surface microstructure for increasing the effective electrical surface by a factor of at least 102.

Furthermore, a material coating, for example a collagen or Fibronectin coating, that has a positive influence on acclimation is preferably provided.

Particularly advantageous embodiments ensue from the realization that, in practice, the best-suited location for fixing the line is not in a fixed position relationship to the vessel location that is best suited for stimulation. This gives rise to the consideration of making the effective electrical part of the arrangement freely positionable, within certain limits, with respect to the mechanical fixing. This is usefully realized by the provision of separate carriers for the electrodes, on the one hand, and the fixing element(s), on the other hand, which carriers can move relative to one another during the positioning of the electrode line, and whose position is set after the optimum position for the fixing element and the electrodes has been determined.

The position setting can be effected by, for example, crimping or a device similar to a collet chuck in the region of the plug.

BRIEF DESCRIPTION OF THE DRAWINGS

Advantageous embodiments of the invention are characterized in the dependent claims, and are described in detail below with the description of the preferred embodiment, with reference to the figures, which show in:

FIGS. 1, 1a, 1b schematic representations of a vessel electrode line according to a first embodiment of the invention, in a side view and front views, respectively, of the distal end in two modifications;

FIGS. 5, 5a a schematic representation of a vessel electrode line according to a fifth embodiment;

FIGS. 6, 6a a schematic representation of a vessel electrode line according to a sixth embodiment;

DETAILED DESCRIPTION OF THE INVENTION

Figure 1B:
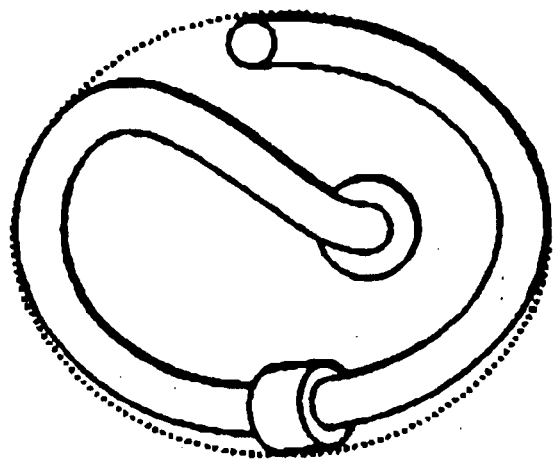
Figure 1A:
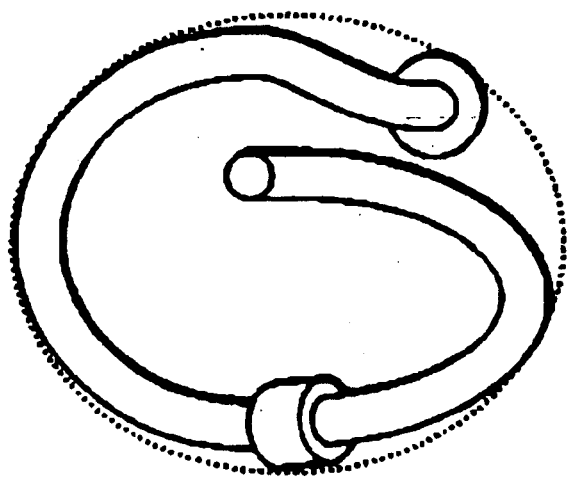

FIGS. 1, 1a and 1b show a vessel electrode line 10 having a base body 11, which receives the electrode supply lines (not shown), a plug 12 and two ring electrodes 13, 14. The front (more distal) ring electrode 13 is spaced about 25 mm from the distal end of the line, at which a Ptlr X-ray marker segment 15 is provided, and has a diameter of 2 mm and a length of 2 mm. The rear (more proximal) electrode 14 is spaced between 60 and 80 mm from the front electrode, and has a diameter of 2.4 mm and a length of 3 mm.

The distal section 11a of the base body 11 has a nearly sinusoidal or S-shaped curvature that is elastically preshaped by means of a core of tempered steel MP35N, and also has an elliptical helical shape, which can be seen in FIGS. 1a and 1b (in two course variations), respectively. The maximum lateral extension of the electrode line in this region is predetermined to match the diameter of the vessel provided as the area of application, and is about 8 mm for a coronary-sinus electrode line. The elasticity of the line is predetermined by a suitable selection of the thickness and material-treatment conditions of the steel core such that the line can be readily extended by the guide wire used during the implantation, and, after the guide wire has been removed, the line exerts sufficient pressure on the vessel wall to fix the position in the illustrated configuration without significantly widening the vessel.

Figure 2:
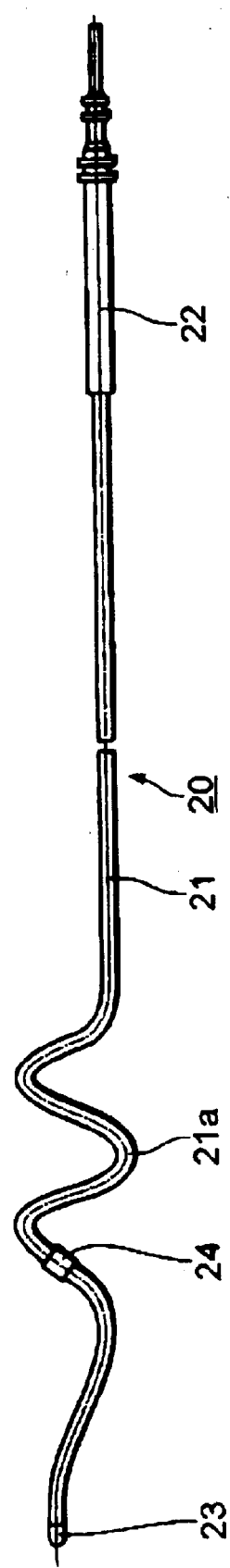
FIG. 2 a schematic representation, in a side view, of a vessel electrode line according to a second embodiment.

FIG. 2 shows a further vessel electrode line 20, which has a base body 21, a plug 22 and a point electrode 23, and a ring electrode 24, which are spaced about 30 mm from one another. Also in this case, a sinusoidal curvature and helical shape are imposed in the region 21a of the line 20, which extends over a length of about 60 mm; the line exhibits a gentle course near the peak electrode and does not assume higher gradients until close to the position of the ring electrode. The curved section includes nearly two sinus periods and turns around the jacket of the elliptical cylinder describing the helix.

Figure 3:
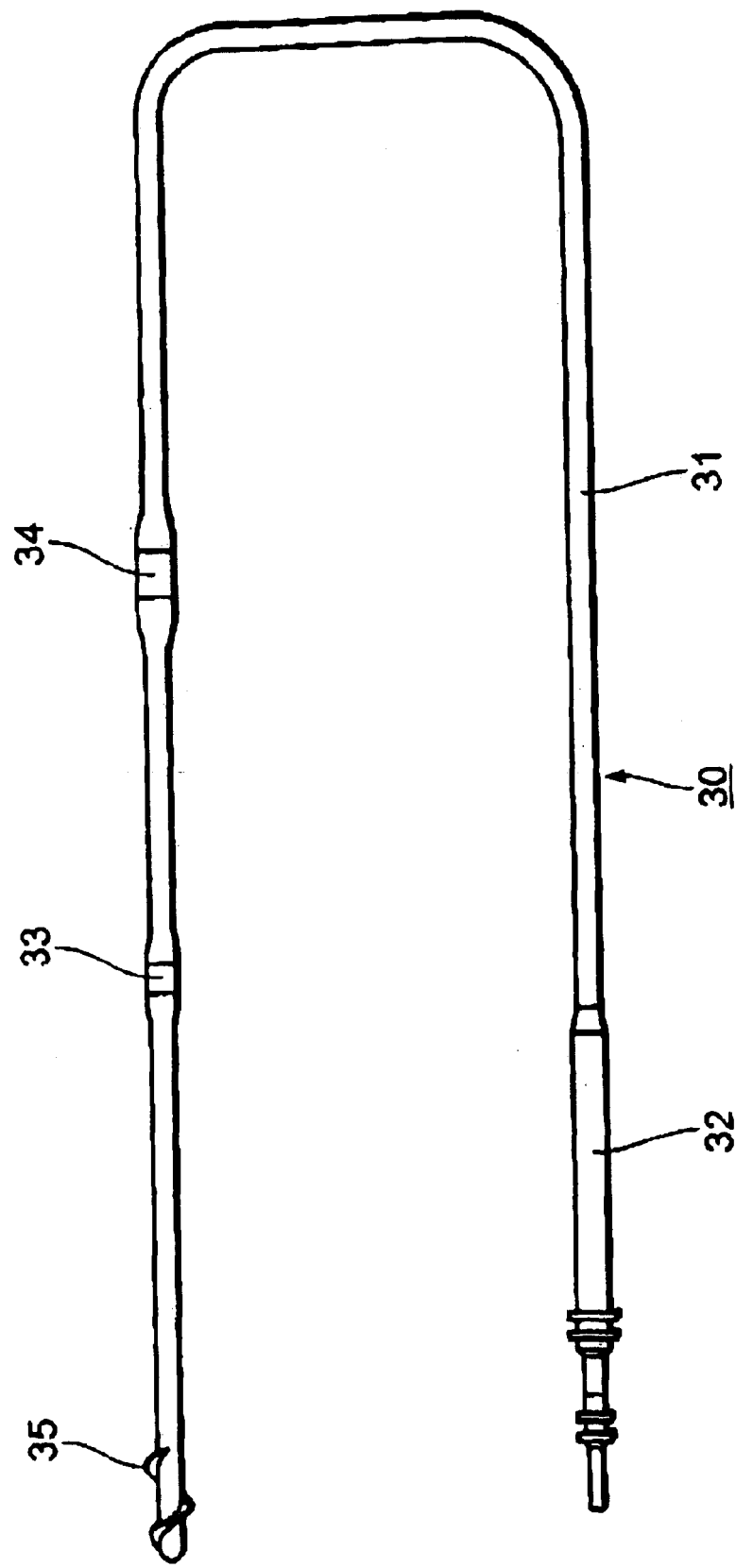
FIG. 3 a schematic representation of a vessel electrode line according to a third embodiment.

FIG. 3 shows a vessel electrode line 30, which has a base body 31 and a plug 32 and extends in the distal end section. The line 30 has two ring electrodes 33 and 34, which have diameters of 2 and 2.4 mm, respectively, and lengths of 2 and 3 mm, respectively. The electrode 33 closer to the distal line end is spaced 75 mm from the end, and the spacing between the two electrodes is 25 mm.

A worm helix 35, which comprises silicon polymers, is about 5 mm long and has two turns, and is joined to the distal end of the base body 31; the helix increases the total diameter of the line to about 3 mm in this region. During the implantation, the line is guided such that the "thread" at the tip enters the mouth of a lateral vessel, and is subsequently screwed in there by means of a corresponding rotation of the guide wire. Because of the pronounced flexional elasticity of the line, after it is fixed, its end region is tensed in the manner of an arch from the mouth of the lateral vessel to the opposite wall of the main vessel (e.g. the coronary sinus), so the electrodes are in contact with the vessel wall without an excessive local pressure being exerted on the wall.

Figure 4:
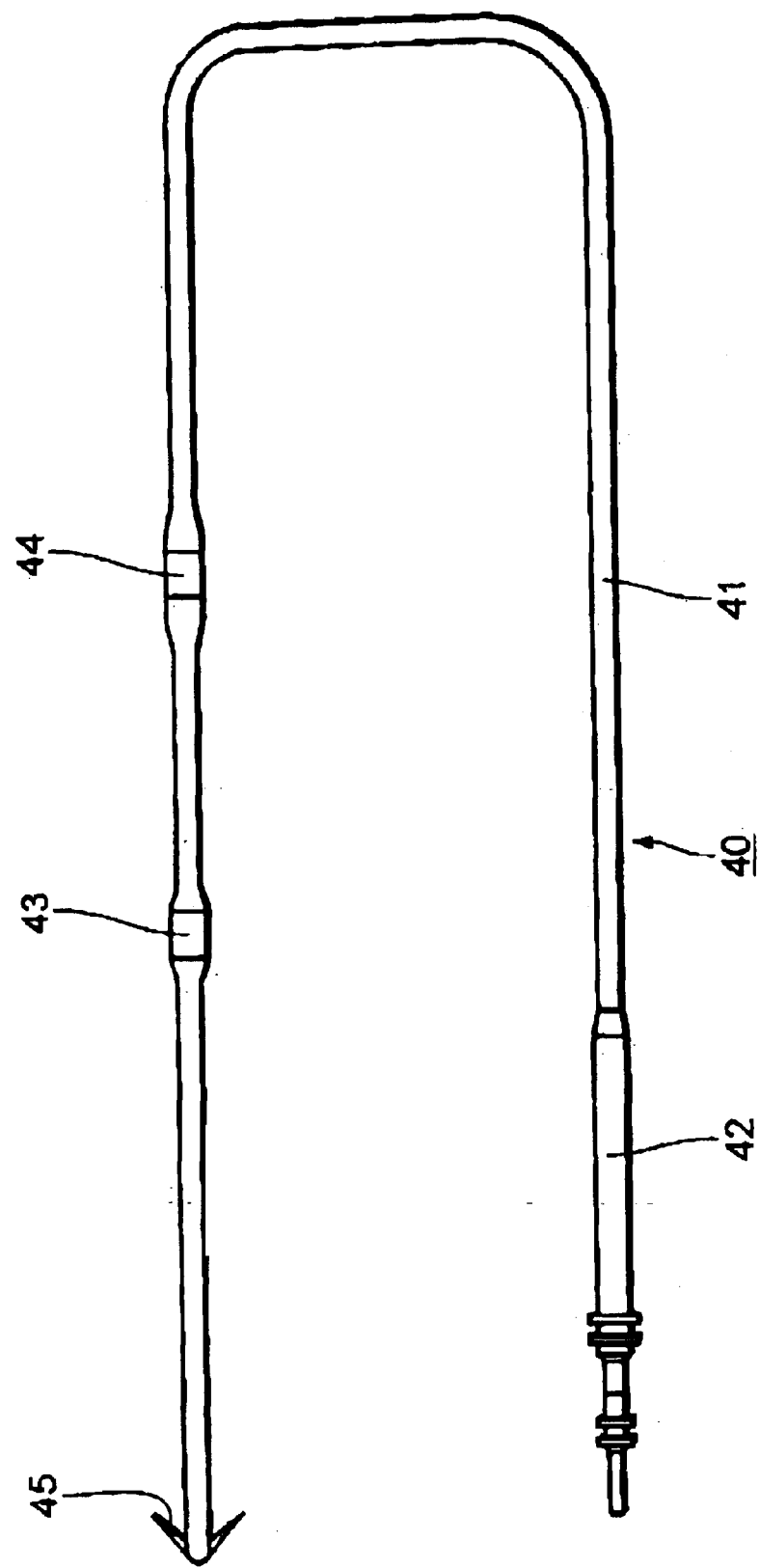
FIG. 4 a schematic representation of a vessel electrode line according to a fourth embodiment.

FIG. 4 shows a further vessel electrode line 40, whose base body 41 extends from the plug 42 to the distal end. The line 41 has two ring electrodes 43 and 44, which have respective diameters of 2 and 2.4 mm and are each 3 mm long. The electrode 43, which is located closer to the distal line end, is spaced 50 to 60 mm from the end, and the two electrodes are spaced 30 to 40 mm apart.

At the distal end, plastic fins or barbs 45 (preferably comprising the same material as the base body, i.e., normally a silicon polymer) are formed onto the base body. The fins 45 have a pronounced acute-angle shape, and are longer than similar anchoring elements of intracardiac electrode lines, yet are flexible. The line is guided by the guide wire such that the fins catch in a vessel branch or the mouth of a lateral vessel, thus fixing the electrodes in a suitable position relative to the wall of the vessel provided for the attachment, especially the coronary sinus.

Figure 5:
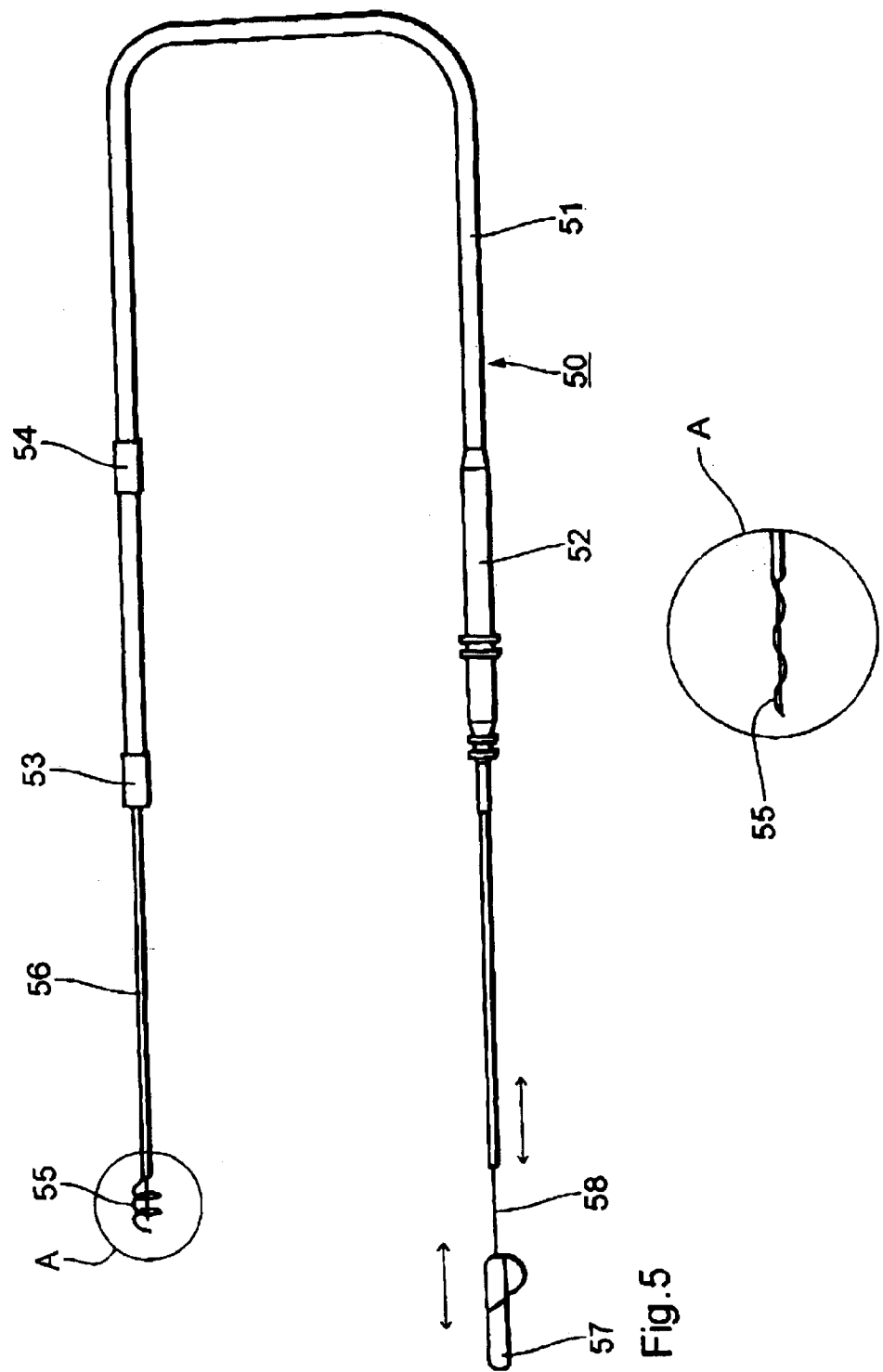

FIGS. 5 and 5a schematically show a further vessel electrode line 50.

With respect to the arrangement of the base body 51, the plug 52 and the electrodes 53, 54, this arrangement is equivalent to the arrangements according to FIG. 3 or 4, so the description is not repeated here. In this instance, however, the base body 51 is embodied such that it receives, in an axially-displaceable manner, a fixing-element support body 56 that is a few centimeters longer than the base body. A highly-elastic helix 55 comprising a biocompatible metal (such as an NiTi alloy) or plastic is secured to the distal end of the support body. The support body 56 is also hollow, so a guide wire 58 having a two-part hand grip 57 mounted at its proximal end can be inserted into it.

The guide wire 568 engages a correspondingly-embodied end of the elastic helix 55, so the helix can be stretched with respect to the fixing-element support body 56 through the advance of the guide wire 58, as can be seen in the section A from FIG. 5 in FIG. 5a.

This permits an easy insertion of the line 50 with the stretched helix 55. After the desired positioning location has been reached, the helix is relaxed by the retraction of the guide wire, and assumes its preset shape, in which its diameter is adapted to the inside dimensions of the vessel such that it rests against the vessel wall under low pressure.

The electrodes 53, 54 can then be optimally positioned in a relatively large adjustment region through the axial displacement of the base body 51 on the fixing-element support body 56 by means of the second part of the hand grip 57. Finally, after the positioning is complete, the position of the base body relative to the fixing-element support body is set (in a manner described in detail below), and the proximal end of the support body 56, which still projects beyond the plug pin 52, is separated, thereby ending the implantation of the line 50.

Figure 6:
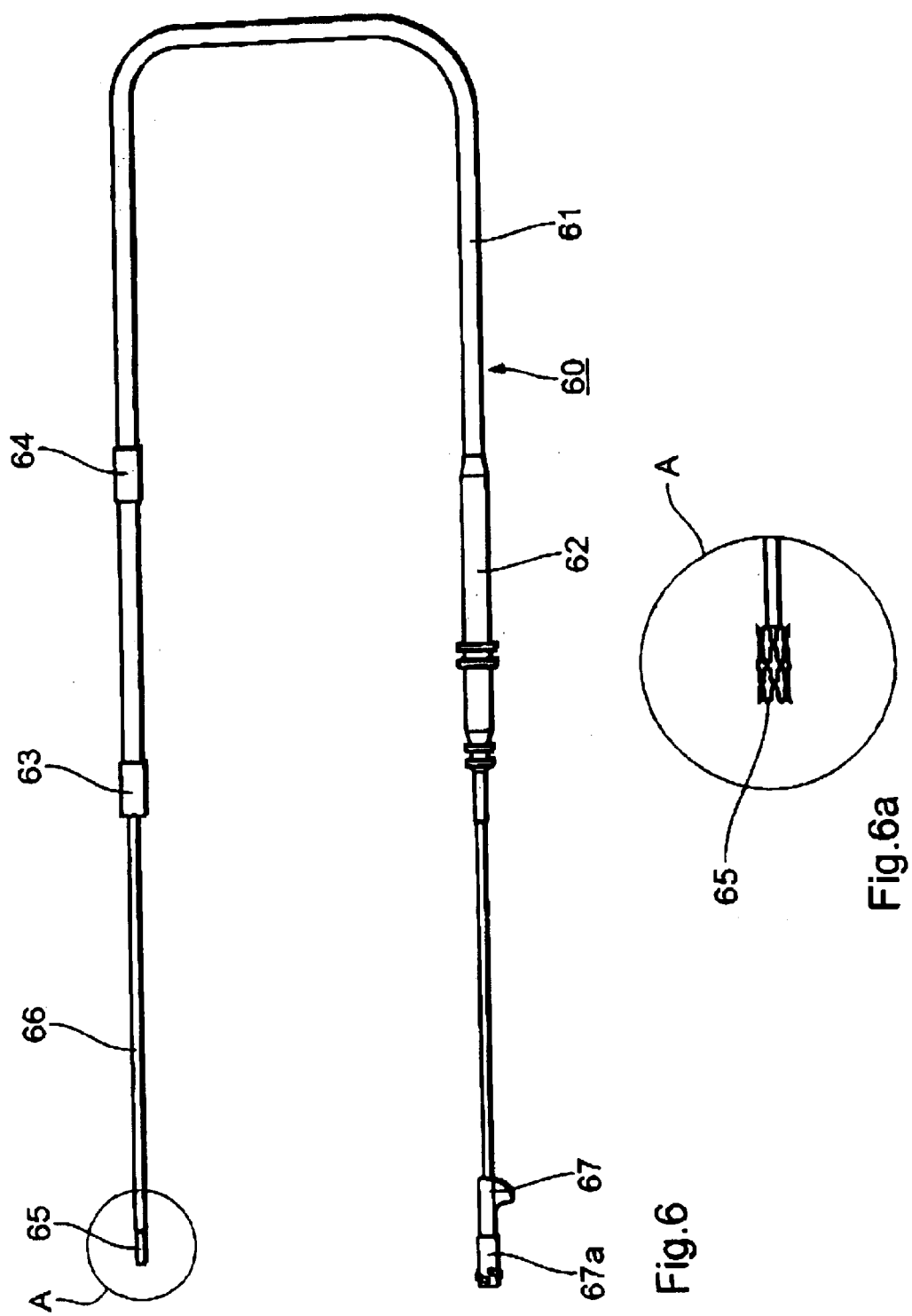

FIGS. 6 and 6a show a vessel electrode line 60, which is similar in design and function to the above-described line according to FIG. 5, but is, however, provided with a tubular fixing element 65 that can be expanded in the manner of a stent after insertion, and comprises a Ti alloy, in place of an elastic helix. Here, the hand grip 67 merely serves to displace the fixing-element support body 66 relative to the base body 61. It additionally has a Luer-lock connector 67a for a connection to a fluid source (not shown), which is required for expanding the fixing element 65 through balloon dilation in a known manner. The cutout A in FIG. 6a shows the expanded state.

Figure 7:
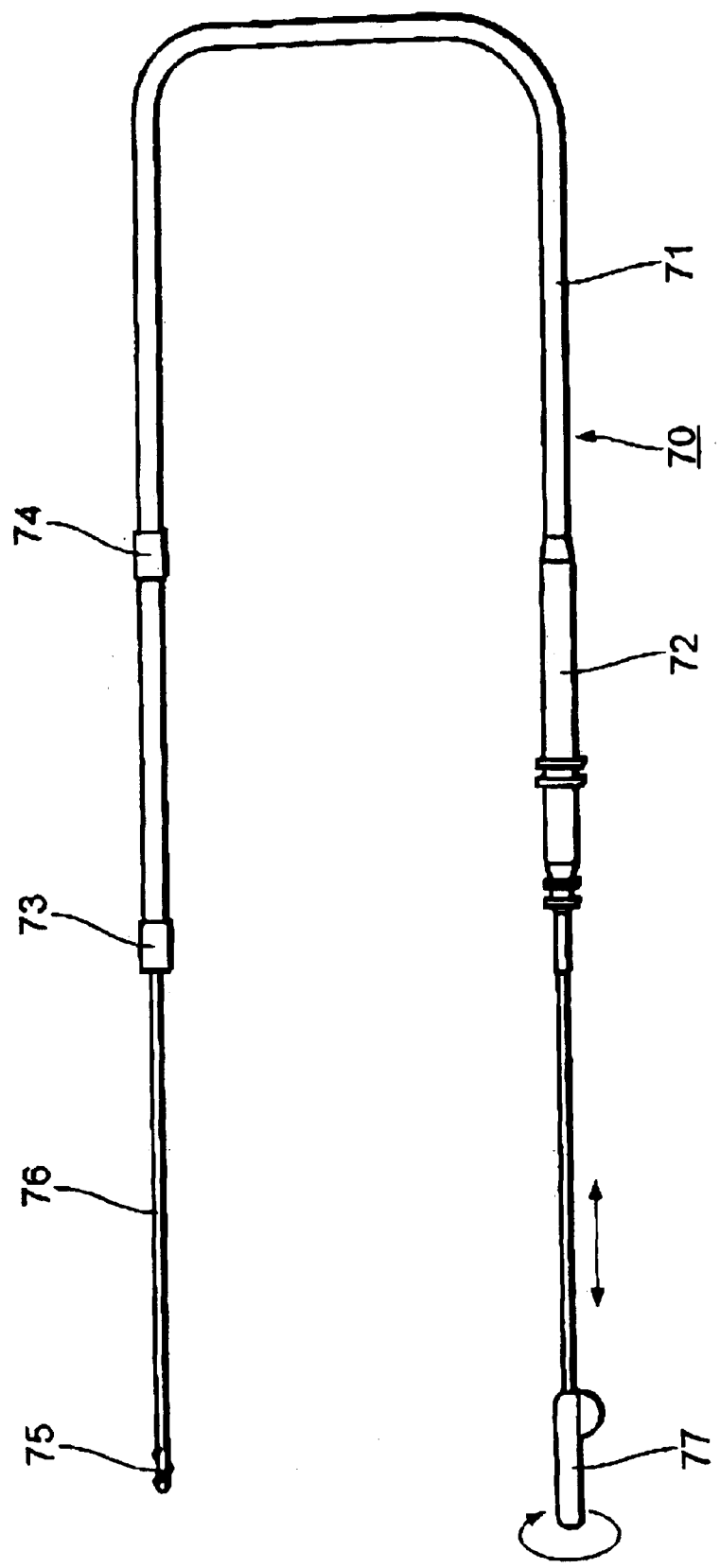
FIG. 7 a schematic representation of a vessel electrode line according to a seventh embodiment.

FIG. 7 shows a vessel electrode line 70, which is similar to the embodiment according to FIG. 3, but in which—as in the arrangements according to FIGS. 5 and 6—a support body 76 that is received in the line base body 71 and can be axially displaced with respect to the base body is provided for the worm-like screw-in helix 75; a hand grip 77 for displacing the support body 76 and screwing in the worm helix 76 is mounted to the proximal end of the support body.

Figure 8A:
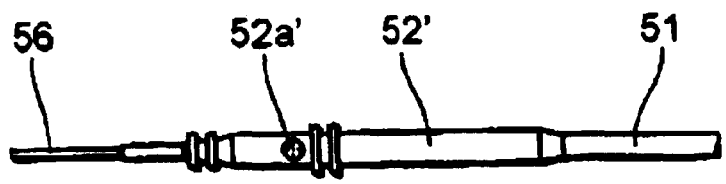
FIGS. 8a–8d schematic representations of different embodiments of a detail in the vessel electrode lines of the type shown in FIGS. 5 through 7.
Figure 8B:
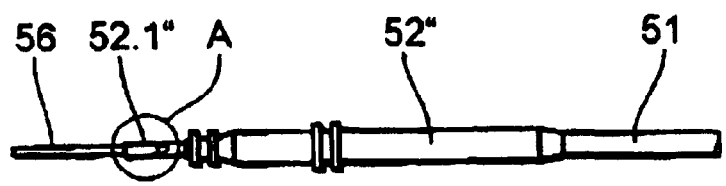
Figure 8C:
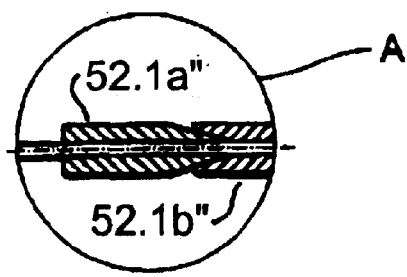

FIGS. 8a through 8d are schematic representations of different embodiments of an essential detail in the vessel electrode lines of the type shown in FIGS. 5 through 7, namely the means for setting the position of the fixing-element support body relative to the base body. In FIG. 8a, a stud screw 52a that acts on the fixing-element support body 56 is provided in the plug 52' for this purpose; in FIG. 8b, the inside plug pin 52.1' of a modified plug 52" is formed from two parts 52.1a' and 52.1b", which cooperate in the manner of a collet chuck, as can best be seen in the cross-sectional representation of the cutout A from FIG. 8b in FIG. 8c.

Figure 8D:
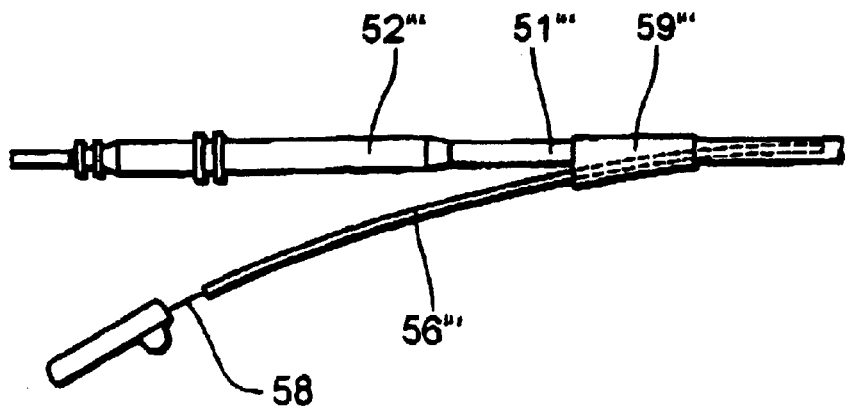

Finally, in the embodiment according to FIG. 8d, the fixing-element support body 51''' is provided, distally from the plug 52''', with a branch element 59''' that is known per se from branched electrode lines, and in which the fixing-element support body 56''' (and, with it, the guide wire 58) is threaded laterally into the base body 51'''. After the positioning has been effected, a ligature serves as the securing means.

The invention is not limited to the above-described, preferred embodiments. Rather, numerous variations are possible that make use of the illustrated solution, even in different embodiments.

Hence, the embodiments shown in FIGS. 1 and 2 can be modified such that the distal end is not helical, but has an essentially coplanar preset shape, or a sinusoidal or meandering predetermined shape that spans two orthogonal planes. The shape of a screw tip or barbs in the manner of the embodiments according to FIG. 3 or 4 can also be modified in numerous ways, taking into consideration the specifics of the application site.

What is claimed is:

1. A vessel electrode line for at least one of pacemaker stimulation and sensing cardiac actions in a region of an atrium, comprising: a base body; at least one electrode supply line received in the base body; at least one electrode mounted on the base body and having an effective diameter nearly identical to the diameter of the base body; and a fixing element that essentially does not act as an electrode, and which has at least a partial insulating surface, adapted to be positioned in a secondary vessel for fixedly positioning the at least one electrode with respect to a main vessel wall, the lateral extension of the fixing element being matched to the diameter of the secondary vessel, the base body or fixing element having a flexional elasticity to bring the at least one electrode into close contact with the wall of the main vessel when the fixing element is positioned in the secondary vessel.

2. The vessel electrode line according to claim 1, characterized in that the fixing elements (11a; 21a) have an essentially coplanar, sinusoidal section of the base body (11; 21) or a section of the base body that is elastically pre-shaped in a helical form on the jacket surface of a cylinder having an elliptical base.

3. The vessel electrode line according to claim 2, characterized in that the section (11a; 21a) that was pre-shaped in a sinusoidal or helical form for fixing the line against the vessel wall of the coronary sinus through elastic pressure has a lateral extension of two to five times the diameter of the base body (11; 21), particularly from 5 to 10 mm, and its elasticity is matched to the elasticity of the vessel wall.

4. The vessel electrode line according to claim 2 or 3, characterized in that the segment (21a) that was pre-shaped in a sinusoidal or helical form includes more than one sinus period or more than one complete turn around the cylinder jacket.

5. The vessel electrode line according to claim 1, characterized in that the fixing element is provided in the distal end region of the base body for fixing the line in the coronary sinus or in a secondary vessel of the coronary sinus, said fixing element having a lateral extension of about 3 mm.

6. The vessel electrode line according to claim 5, characterized in that a plastic worm-thread segment that surrounds the distal end of the base body and has one to three turns, is provided as the fixing element.

7. The vessel electrode line according to claim 5, characterized in that a plurality of plastic fins (45) that are resiliently inclined toward the proximal end with respect to the longitudinal axis of the base body (41) are provided as the fixing elements.

8. The vessel electrode line according to claim 5, characterized in that an elastic helix (55) is provided as the fixing element, the helix's diameter being at the most equal to the diameter of the base body during the insertion, when it is in a stretched state due to an insertion aid (58), and being larger than that of the base body in the relaxed state.

9. The vessel electrode line according to claim 5, characterized in that an expandable, tubular element (65) is provided as the fixing element, the element's diameter being at the most equal to the diameter of the base body before and during the insertion, and larger than that of the base body in an expanded, final state.

10. The vessel electrode line according to claim 8 or 9, characterized in that at least a part of the surface of the elastic helix (55) or the tubular element (65) is non-conductive.

11. The vessel electrode line according to one of claims 5 through 10, characterized in that the fixing element (55; 65; 75) is mounted to a fixing-element support body (56; 66; 76) that is axially displaceable with respect to the base body, and whose axial position on the base body can be fixed.

12. The vessel electrode line according to claim 5, characterized in that the fixing element is flexible.

13. The vessel electrode line according to claim 1, characterized in that the electrode or the most distal of a plurality of electrodes is spaced between 30 and 80 mm from the distal end of the base body.

14. The vessel electrode line according to claim 1, characterized by two electrodes on the base body spaced between 25 and 80 mm from one another.

15. The vessel electrode line according to claim 1, characterized in that the electrode is between 2 and 3 mm long and has a geometric surface area between 10 and 25 mm$^2$.

16. The vessel electrode line according to claim 1, characterized by a material coating, comprising a collage or fibronectin coating, that has a positive influence on the acclimation in the surrounding tissue.

* * * * *